(12) United States Patent
Liphardt et al.

(10) Patent No.: US 7,468,794 B1
(45) Date of Patent: *Dec. 23, 2008

(54) ROTATING COMPENSATOR ELLIPSOMETER SYSTEM WITH SPATIAL FILTER EQUIVALENT

(75) Inventors: Martin M. Liphardt, Lincoln, NE (US); Blaine D. Johs, Lincoln, NE (US); Craig M. Herzinger, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 649 days.

This patent is subject to a terminal disclaimer.

(21) Appl. No.: 11/204,929

(22) Filed: Aug. 15, 2005

Related U.S. Application Data

(63) Continuation-in-part of application No. 10/178,723, filed on Jun. 24, 2002, now Pat. No. 6,950,182, and a continuation-in-part of application No. 09/864,840, filed on May 24, 2001, now Pat. No. 6,456,376, said application No. 10/178,723 is a continuation-in-part of application No. 09/845,548, filed on Apr. 30, 2001, now Pat. No. 6,585,128, and a continuation-in-part of application No. 09/419,794, filed on Oct. 18, 1999, now Pat. No. 6,549,282, application No. 11/204,929, which is a continuation-in-part of application No. 10/699,540, filed on Nov. 1, 2003, now Pat. No. 7,158,231, which is a continuation-in-part of application No. 09/945,962, filed on Sep. 4, 2001, now Pat. No. 7,075,649, and a continuation-in-part of application No. 09/496,011, filed on Feb. 1, 2000, now Pat. No. 6,353,477.

(60) Provisional application No. 60/300,714, filed on Jun. 26, 2001.

(51) Int. Cl.
 *G01J 4/00* (2006.01)

(52) U.S. Cl. ................................................ 356/369
(58) Field of Classification Search ............... None
 See application file for complete search history.

(56) References Cited

U.S. PATENT DOCUMENTS

| | | | |
|---|---|---|---|
| 3,905,675 A | 9/1975 | McCraker | 350/17 |
| 4,053,232 A | 10/1977 | Dill et al. | 356/369 |
| 4,877,960 A | 10/1989 | Messerschmidt et al. | 250/341 |
| 4,996,120 A | 2/1991 | Smothers et al. | 430/2 |
| 5,032,734 A | 7/1991 | Orazio, Jr. et al. | 250/572 |
| 5,148,323 A | 9/1992 | Campbell et al. | 359/738 |
| 5,329,357 A | 7/1994 | Bernoux et al. | 356/369 |
| 5,373,359 A | 12/1994 | Woollam et al. | 356/328 |
| 5,414,559 A | 5/1995 | Burghardt et al. | 359/623 |
| 5,426,506 A | 6/1995 | Ellingson et al. | 356/369 |
| 5,504,582 A | 4/1996 | Johs et al. | 356/369 |
| 5,517,312 A | 5/1996 | Finarov | 356/386 |
| 5,521,706 A | 5/1996 | Green et al. | 356/369 |
| 5,608,526 A | 3/1997 | Piwonka-Corle et al. | 356/369 |

(Continued)

Primary Examiner—Gregory J Toatley, Jr.
Assistant Examiner—Juan D Valentin
(74) Attorney, Agent, or Firm—James D. Welch

(57) ABSTRACT

Application of a spatial filter equivalent constructed from a converging lens and an optical fiber in rotating compensator ellipsometer systems, after a sample system. The purpose is to eliminate a radially outer annulus of a generally arbitrary Profile beam that presents with low intensity level irregular content, so that electromagnetic beam intensity is caused to quickly decay to zero as a function of radius.

29 Claims, 11 Drawing Sheets

U.S. PATENT DOCUMENTS

| | | | |
|---|---|---|---|
| 5,666,201 A | 9/1997 | Johs et al. | 356/369 |
| 5,684,642 A | 11/1997 | Zumoto et al. | 359/740 |
| 5,796,521 A | 8/1998 | Kahlert et al. | 359/619 |
| 5,859,424 A | 1/1999 | Norton et al. | 250/226 |
| 5,872,630 A | 2/1999 | Johs et al. | 356/369 |
| 5,877,859 A | 3/1999 | Aspnes et al. | 356/364 |
| 5,889,593 A | 3/1999 | Bareket | 356/445 |
| 5,910,842 A | 6/1999 | Piwonka-Corle et al. | 356/369 |
| 5,917,594 A | 6/1999 | Norton | 356/327 |
| 5,946,098 A | 8/1999 | Johs et al. | 356/364 |
| 5,963,325 A | 10/1999 | Johs et al. | 356/364 |
| 5,963,327 A | 10/1999 | He et al. | 356/369 |
| 6,084,674 A | 7/2000 | Johs et al. | 356/364 |
| 6,100,981 A | 8/2000 | Johs et al. | 356/364 |
| 6,134,012 A | 10/2000 | Aspnes et al. | 356/369 |
| 6,141,102 A | 10/2000 | Johs et al. | 356/364 |
| 6,184,984 B1 | 2/2001 | Lee et al. | 356/369 |
| 6,321,601 B1 | 11/2001 | Maris | 73/657 |

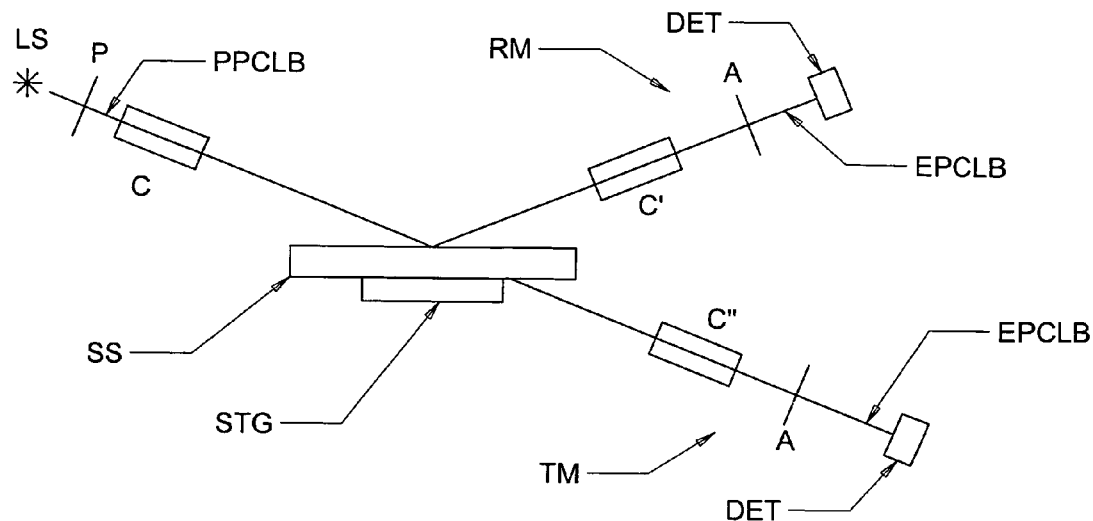
FIG. 1a₁
PRIOR ART
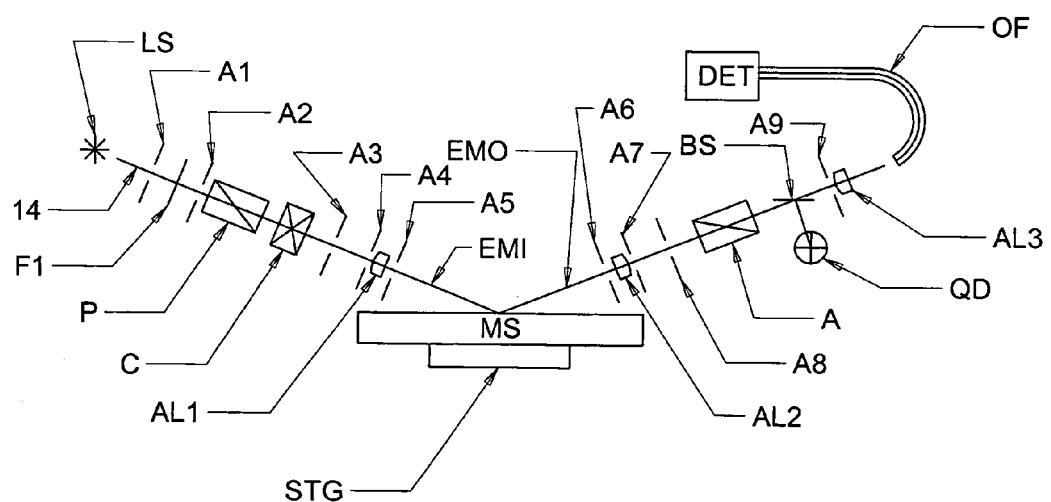
FIG. 1a₇

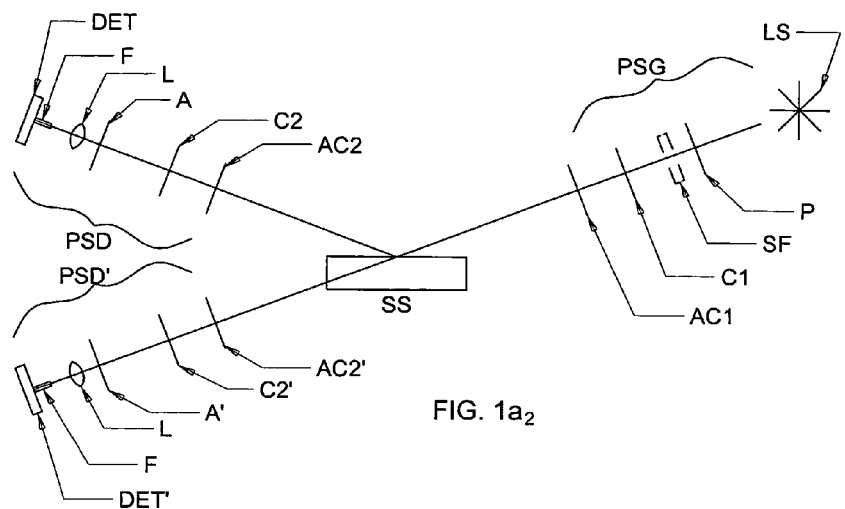
FIG. 1a₂
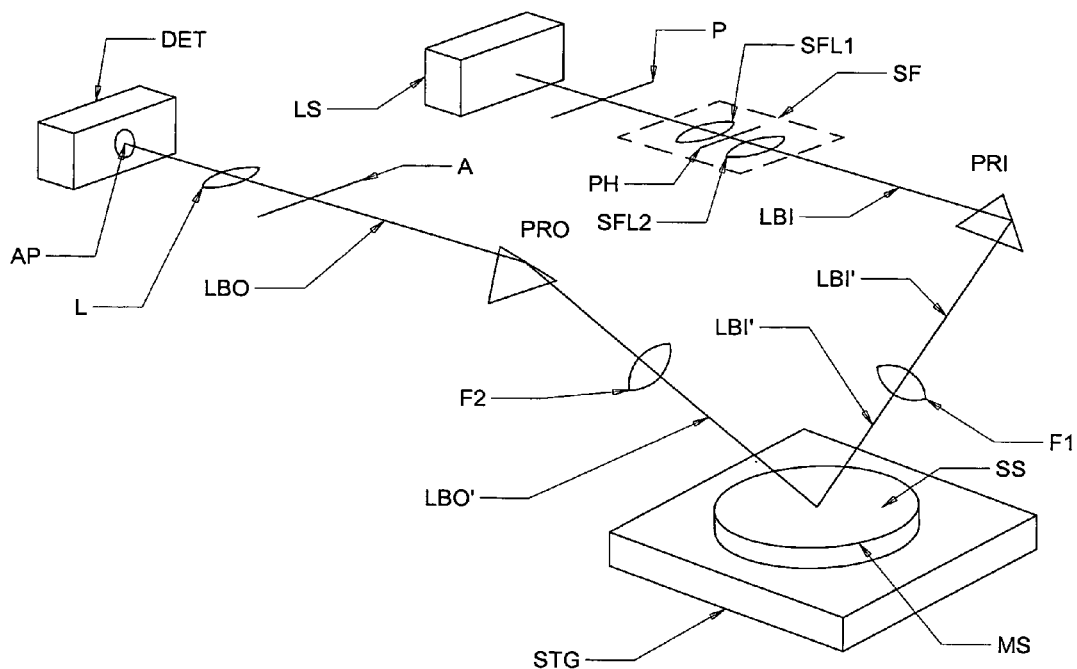
FIG. 1a₃

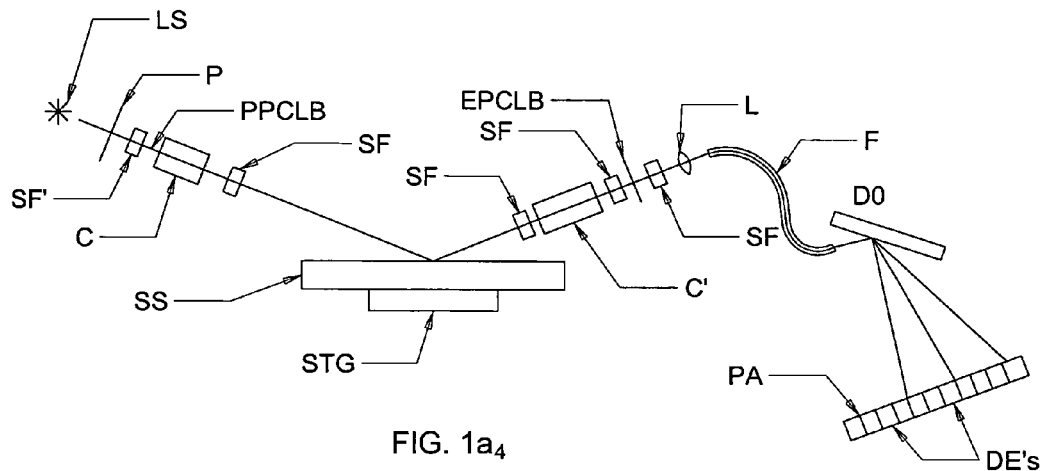
FIG. 1a₄
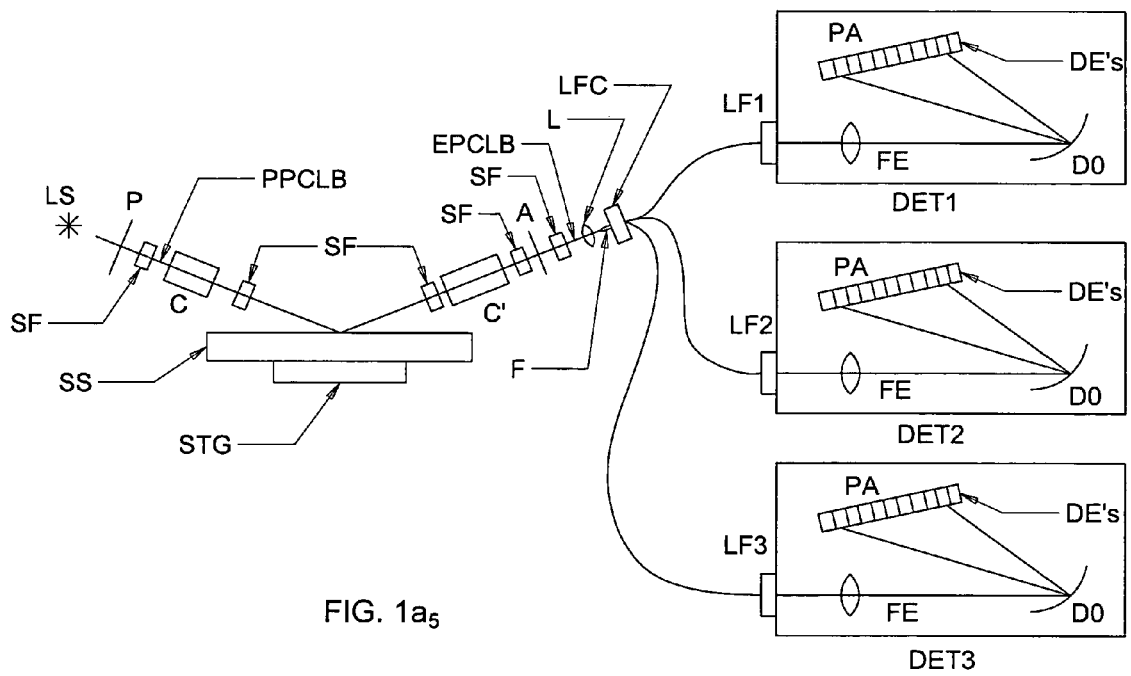
FIG. 1a₅

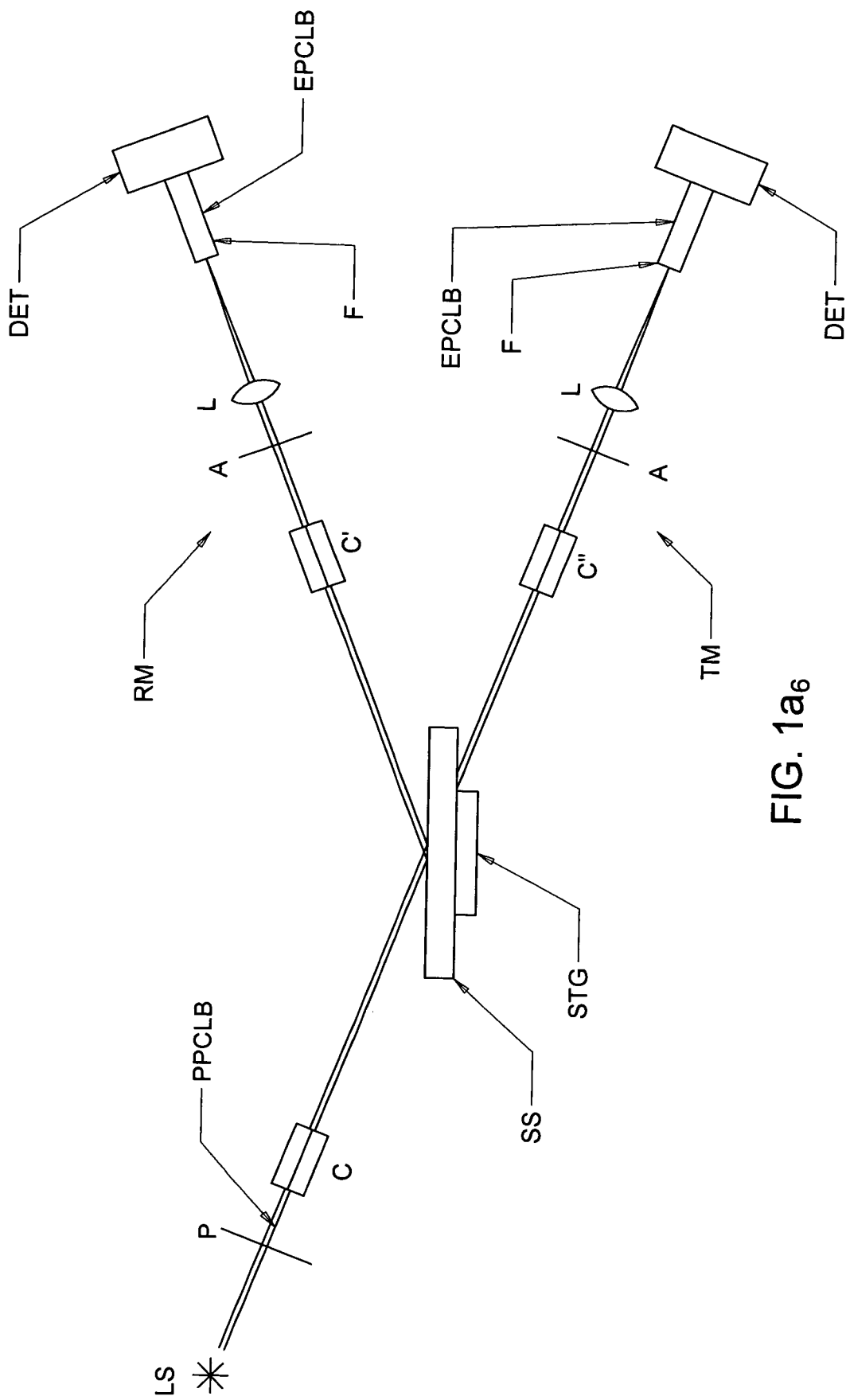
FIG. 1a₆

$$d = 2h\left(\frac{1}{\tan(\alpha)} + \tan(\phi)\right), \text{where } \phi = \alpha + \sin^{-1}\left(\frac{\sin(90 - \alpha)}{n}\right)$$

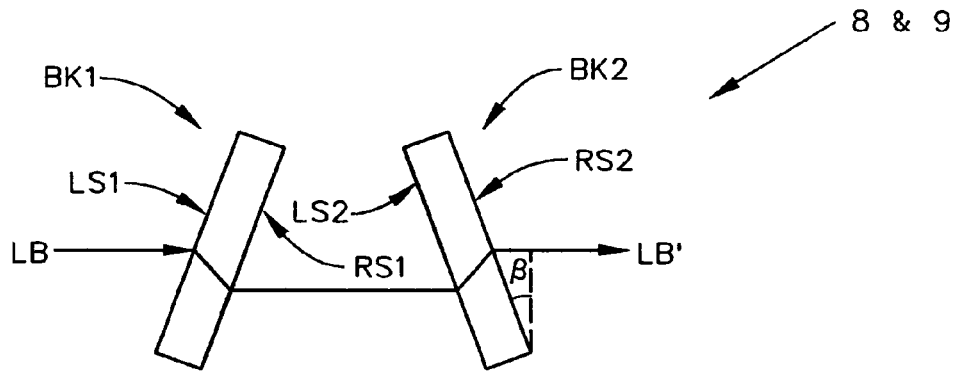
FIG. 5k₁
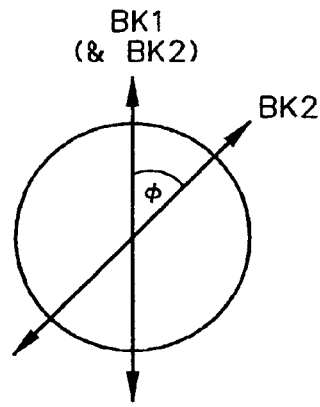
FIG. 5k₂
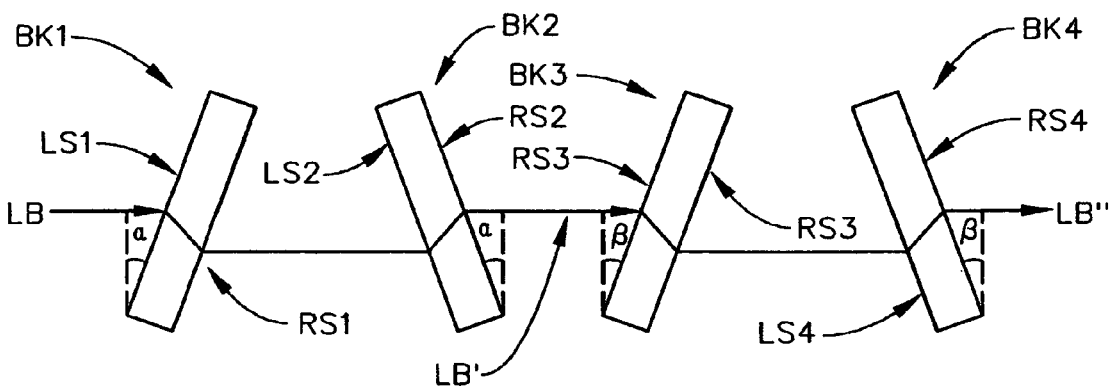
FIG. 5l₁

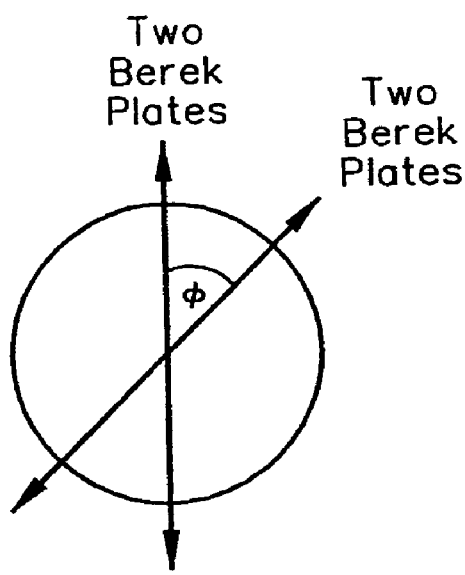
FIG. 5l$_2$
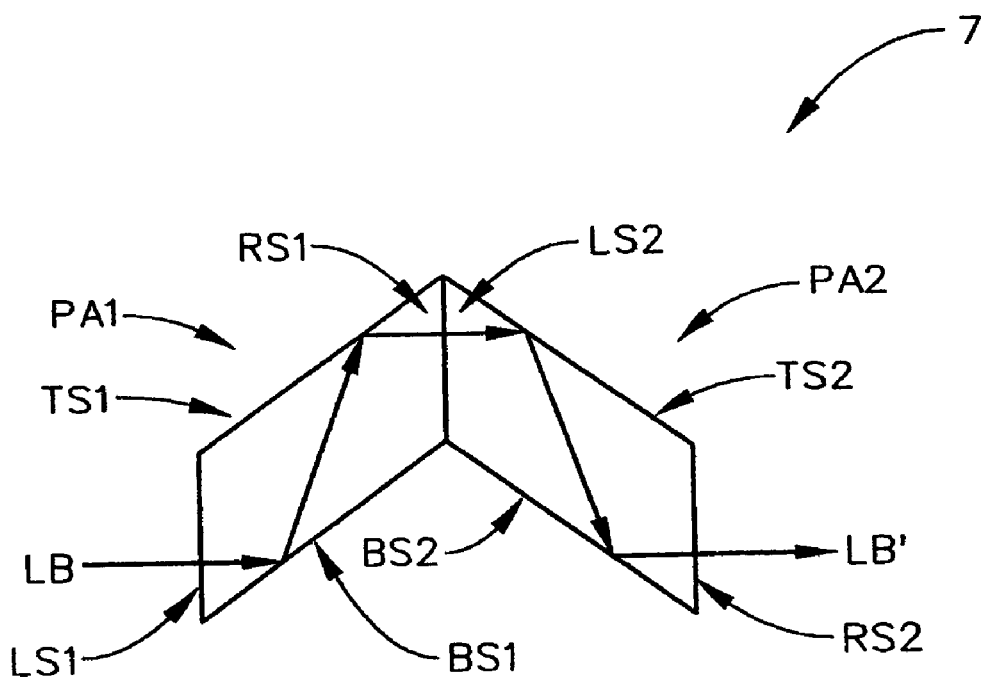
FIG. 5m

ROTATING COMPENSATOR ELLIPSOMETER SYSTEM WITH SPATIAL FILTER EQUIVALENT

This application is a CIP of Allowed application Ser. No. 10/178,723, Filed Jun. 24, 2002 now U.S. Pat. No. 6,950,182; and therevia of application Ser. No. 09/864,840 Filed May 24, 2001, (now U.S. Pat. No. 6,456,376; and of Ser. No. 09/419,794 Filed Oct. 18, 1999 now U.S. Pat. No. 6,549,282; and of Ser. No. 09/845,548 Filed Apr. 30, 2001 now U.S. Pat. No. 6,585,128; and via the above Claims benefit of 60/300,714 Filed Jun. 26, 2001. This application is further a CIP of application Ser. No. 10/699,540 Filed Nov. 1, 2003 now U.S. Pat. No. 7,158,231; which is a CIP of Ser. No. 09/945,962 Filed Sep. 4, 2001 now U.S. Pat. No. 7,075,649; and via the 540 application is a CIP of Ser. No. 09/496,011 Filed Feb. 1, 2000, (now U.S. Pat. No. 6,353,477), which depended from application Ser. No. 09/246,888 Filed Feb. 8, 1999, (now U.S. Pat. No. 6,084,675). Further, via the Ser. No. 09/246,888 application, this application is a CIP of application Ser. No. 08/912,211 Filed Aug. 15, 1997, (now U.S. Pat. No. 5,872,630), which was a CIP from application Ser. No. 08/530,892 Filed Sep. 20, 1995, (now U.S. Pat. No. 5,666,201); which was a CIP of application Ser. No. 08/618,820 Filed Mar. 20, 1996, (now U.S. Pat. No. 5,706,212). This application is further a CIP, via application Ser. Nos. 10/178,723, and 09/846,840, of application Ser. Nos. 09/225,118, Filed Jan. 4, 1999, (now U.S. Pat. No. 6,084,674); 09/223,822, Filed Jan. 4, 1999, (now U.S. Pat. No. 6,118,537); 09/232,257, Filed Jan. 19, 1999, (now U.S. Pat. No. 6,141,102); 09/225,371, Filed Jan. 4, 1999, (now U.S. Pat. No. 6,100,981); 09/225,076, Filed Jan. 4, 1999, (now U.S. Pat. No. 5,963,325); which depended from application Ser. No. 08/997,311 Filed Dec. 23, 1997, (now U.S. Pat. No. 5,946,098). This application is also CIP of Co-Pending application Ser. Nos. 10/928,429 Filed Aug. 27, 2004; and therevia of 09/583,229 Filed May 30, 2000; and therevia of Ser. No. 09/419,794 (now U.S. Pat. No. 6,549,282); and of Co-Pending application Ser. Nos. 10/613,051 Filed Jul. 7, 2003; and of 10/699,540 Filed Nov. 1, 2003; and of Ser. No. 10/425,801 Filed Apr. 29, 2003. And this application Claims Benefit, via the above, of Provisional Applications 60/473,616 Filed May 28, 2003; 60/553,032 Filed Mar. 15, 2004; 60/517,566 Filed Nov. 6, 2003; 60/572,204 Filed May 18, 2004; 60/527,554 Filed Dec. 6, 2003; 60/527,638 Filed Dec. 8, 2003; 60/576,466 Filed Jun. 3, 2004; and 60/498,479 Filed Aug. 28, 2003.

TECHNICAL FIELD

The present invention relates to rotating compensator ellipsometer systems, and more particularly to spectroscopic rotating compensator ellipsometer systems which comprises a focusing lens and optical fiber after an investigated sample system and before a detector.

BACKGROUND

Not limited to, but particularly in the case where an electromagnetic beam is utilized to investigate a sample system which presents with a varying depth surface topology, it is important to provide an electromagnetic beam of a known lateral dimension and which presents with a relatively simple cross-sectional intensity profile.

It is noted that often electromagnetic beams present with a substantially arbitrary intensity profile, with the highest intensity being located centrally, which intensity generally decreasing as with increasing radius. While an arbitrary beam intensity profile is typically acceptable for use in ellipsometry and related practices, it has been found that once the intensity of a substantially arbitrary profile beam of electromagnetic radiation has decreased to, as an arbitrary example, say 10% of its peak, it does not always continue to decay directly to essentially zero (0.0). Instead, it often presents irregularly as a function of radius, (eg. easily visualized as being generally similar to the Fourier transform of a square wave), and such irregular intensity content can adversely affect ellipsometer performance. The cause of said irregular intensity profile can include such as optical element wavelength dependent diffraction, surface roughness or other non-idealities, and where electromagnetic radiation is provided via an aperture or via the end of a light fiber contained in a cladding, electromagnetic radiation falling outside a geometric image thereof is often of an irregular intensity content.

It would be of benefit, as regards obtaining accurate data from application of ellipsometers and the like systems, if the intensity of an electromagnetic beam could be forced to decay quickly to zero (0.0), rather than demonstrate an irregular intensity profile as a function of radius in an outer annulus region.

With an eye to the present invention, a Search of patents was conducted. Perhaps the most relevant patent identified is No. 5,517,312 to Finarov. Said 312 patent describes application of a scattered light reducing system at the entry to a Detector in a-Rotating Analyzer or Rotating Polarizer Ellipsometer System, which scattered light reducing system consists of two lenses with a pin-hole containing diaphram located midway therebetween, and at the focal lengths of said lenses. Said scattered light reducing system is present after a sample system and processes electromagnetic radiation after it interacts with said sample system. The pinhole is described as serving to reduce scattered light and providing high spatial resolution. Another patent identified is that to Campbell et al., No. 5,148,323. Said 323 patent describes a Spatial Filter in which a pinhole is located other than at the focal length of a converging lens. U.S. Pat. No. 3,905,675 to McCraken describes a Spatial Filter containing system which enables observation of a weak source of electromagnetic radiation in the presence of strong sources thereof. U.S. Pat. No. 5,684,642 to Zumoto et al., describes an optical transmission system for use in fashioning an electromagnetic beam for use in machining materials which combines a Spatial Filter and an Optical Fiber. U.S. Pat. No. 4,877,960 to Messerschmidt et al. is identified as it describes masking energy from outside the target area in a microscope having dual remote image masking.

Continuing, Spectroscopic Rotating Compensator Ellipsometer Systems are also known in the art. And, as mentioned, application a Spatial Filters near a Detector, in the context of Rotating Polarizer and Rotating Analyzer Ellipsometer Systems has been reported, (see U.S. Pat. No. 5,517,312 to Finerov). However, the application of Spatial Filters in Rotating Compensator Ellipsometer Systems, such as the Rotating Compensator Ellipsometer System Claimed in co-owned U.S. Pat. No. 5,872,630, has not here-to-fore been known. Said 630 patent, which is incorporated by reference hereinto and which is co-owned with this application, is disclosed as it describes an ellipsometer system in which an analyzer and polarizer are maintained in a fixed in position during data acquisition, while at least one compensator is caused to continuously rotate.

A patent to Dill et al., U.S. Pat. No. 4,053,232 is disclosed as it describes a Rotating-Compensator Ellipsometer System which operates utilizing monochromatic light.

A patent to Aspnes et al., U.S. Pat. No. 5,877,859 is disclosed as it describes a Broadband Spectroscopic Rotating Compensator Ellipsometer System whrein the Utility is derived from selecting a wavelength range and compensator so that at least one wavelength in said wavelength range has a retardation imposed of between 135 and 225 degrees, and another wavelength in said wavelength range has a retardation imposed which is outside that retardation range.

A patent, U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this patent is not controlling where electromagnetic radiation carrying fiber optics are present.

Further patents of general interest of which the Inventors are aware include those to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertain to ellipsometer systems.

A patent to He et al., U.S. Pat. No. 5,963,327 is also disclosed as it describes a laterally compact ellipsometer system which enables providing a polarized beam of electromagnetic radiation at an oblique angle-of-incidence to a sample system in a small spot area.

In addition to the identified patents, certain Scientific papers are also identified.

A paper by Johs, titled "Regression Calibration Method for Rotating Element Ellipsometers", Thin Solid Films, 234 (1993) is also disclosed as it describes a mathematical regression based approach to calibrating ellipsometer systems.

A Review paper by Collins, titled "Automatic Rotating Element Ellipsometers Calibration, Operation and Real-Time Applications", Rev. Sci. Instrum., 61(8) (1990), is identified for general information.

Even in view of the known art, in the context of rotating compensator ellipsometer systems, a need remains for a system and methodology of its use, which adds spatial filter means before and/or after a sample system, to, for instance, fashion a beam with a radially essentially arbitrary Profile which directly approaches zero intensity. The present invention meets said need.

DISCLOSURE OF THE INVENTION

Rotating Compensator Ellipsometer Systems provide many benefits, (eg. Sample System PSI and DELTA investigation limiting "dead-spots" are not present), but until a co-owned Parent patent to Johs et al., U.S. Pat. No. 5,872,630 taught otherwise, it was generally believed that in the absence of essentially Achromatic "ideal" Compensators, it would be prohibitively difficult and expensive to build, calibrate and utilize a "Spectroscopic" Rotating Compensator Ellipsometer System. This is to be understood in light of the fact that Compensators which are essentially Achromatic, (ie. provide essentially constant retardation over a large range of Wavelengths, such as 190-1000 nanometers), are not generally and economically available as off-the-shelf items. The present invention expands on the utility available from the Spectroscopic Rotating Compensator Ellipsometer System previously taught in the 630 patent. In very general terms the present invention is a rotating compensator ellipsometer system which generates an electromagnetic beam and causes it to impinge upon a sample system, said spectroscopic rotating compensator ellipsometer system comprising, after said sample system, a converging lens and optical fiber which, for instance, serves to attenuate an outer annular region from said electromagnetic beam as it passes therethrough. More specifically, the present invention spectroscopic rotating compensator ellipsometer system is affordable, easy to calibrate and utilize and comprises a Source of a Polychromatic Beam of Electromagnetic Radiation, a Polarizer, a Stage for Supporting a Sample System, an Analyzer, a Dispersive Optics and at least one Photo Array Detector Element System which contains a multiplicity of Detector Elements, which Spectroscopic Rotating Compensator System further comprises at least one Rotatable Compensator(s) positioned at location(s) selected from the group consisting of: (before said stage for supporting a sample system and after said stage for supporting a sample system and both before and after said stage for supporting a sample system). Said present invention Spectroscopic Rotating Compensator Ellipsometer System can also comprise a conventional Spatial Filter System which minimally sequentially comprises:

beam converging at least one lens and/or mirror;
diaphram with a pin hole therein located near the focal length of said beam converging at least one lens and/or mirror; and
beam collimating at least one lens and/or mirror;

such that in use an electromagnetic beam which is caused to interact with said beam converging at least one lens and/or mirror becomes focused on, and at least partially passes through said pin hole in said diaphram, and then becomes recollimated by said second beam at least one collimating lens and/or mirror. Said present invention does, however, comprise a converging lens and optical fiber prior to a detector system.

A present invention spectroscopic rotating compensator based ellipsometer system can comprise addition of an aperture such that the configuration is:

first beam collimating lens;
aperture;
first beam converging at least one lens and/or mirror; diaphram with a pin hole therein located essentially at the focal length of said beam converging at least one lens and/or mirror; and
second beam collimating at least one lens and/or mirror;

and such that, in use, the central portion of the electromagnetic beam which is collimated by said first beam collimating lens is caused to pass through said aperture, become focused on and at least partially pass through said pin hole in said diaphram by said first beam converging at least one lens and/or mirror, and become recollimated by said second beam collimating at least one lens and/or mirror. Said configuration is combined with a Converging Lens and Optical Fiber arrangement.

The present invention can also be considered to be a spectroscopic rotating compensator based ellipsometer system which comprises:

a polarization state generator comprising said Source of a Polychromatic Beam of Electromagnetic Radiation and Polarizer;
means for supporting a sample system; and
a polarization state detector, comprising said Analyzer, a Dispersive Optics and at least one Photo Array Detector Element System which contains a multiplicity of Detector Elements;

with at least one of said polarization state generator and polarization state detector further comprising at least one compensator;

and optionally a conventional spatial filter being present in at least one selection from the group consisting of:

said polarization state generator; and
said polarization state detector;

which spatial filter which sequentially comprises:

first at least one lens and/or mirror;
pin hole containing diaphram; and
second at least one lens and/or mirror;

with the optional inclusion of collimating lens;
aperture;

prior to said first at least one lens and/or mirror;

said pin hole containing diaphram being positioned near the focal points of said first and second at least one lenses or mirrors, such that a collimated electromagnetic beam enters said first at least one lens or mirror, is converged and at least partially passes through said pin hole, and is recollimated by said second at least one lens and/or mirror. Conventional Spatial filter(s) can be present in either the polarization state generator or polarization detector. Said spatial filter can be positioned at a location selected from the group consisting of:

between the source of electromagnetic radiation and the polarizer;
between a compensator and sample system;
between the sample system and a compensator;
between a compensator and analyzer; and
between the analyzer and detector;

said described system being distinguished by comprises a Converging Lens and Optical Fiber arrangement prior to a Detector system.

The present invention is further, in the context of spectroscopic rotating compensator based ellipsometer systems, a method of processing electromagnetic beams to, for instance, eliminate a radially outer annulus thereof, said outer annulus often being comprised of low intensity level irregular content, said method optionally comprising placing at least one conventional spatial filter(s) such that said electromagnetic beam passes therethrough, each present conventional spatial filter sequentially comprising:

aperture;
beam converging at least one lens and/or mirror;
diaphram with a pin hole therein located near the focal length of said beam converging at least one lens and/or mirror; and
beam collimating at least one lens and/or mirror;

such that, in use, an electromagnetic beam which is caused to pass through said aperture, become focused on and at least partially pass through said pin hole in said diaphram by said beam converging at least one lens and/or mirror, and become recollimated by said second beam collimating at least one lens and/or mirror;

said method further comprising including a Converging Lens and Optical Fiber arrangement prior to a Detector system and causing said an electromagnetic beam to interact with a sample and then pass through said converging lens, become focused on and enter said optical fiber before passing to a detector.

Said present invention method can be recited as, in the context of a spectroscopic rotating compensator ellipsometer system which causes a beam of electromagnetic radiation to interact with a sample system, comprising the steps of:

a. providing a beam of electromagnetic radiation;
b. providing a sample system;
c. optionally placing at least one conventional spatial filter(s) in the pathway of said electromagnetic beam such that said electromagnetic beam passes therethrough prior to or after said electromagnetic beam being caused to interact with a sample system;
d. providing a converging lens and optical fiber such that said electromagnetic beam passes through said converging lens, partially passes through said optical fiber and enters a detector, after being caused to interact with a sample system;

the purpose being to eliminate a radially outer annulus of said electromagnetic beam which is comprised of a low intensity level irregular content.

In the preferred present invention Rotating Compensator Ellipsometer System, said at least one Compensator(s) utilized in the present invention can be essentially any available, reasonably priced, off-the-shelf Retardation providing system, including non-Achromatic, Berek-type, Zero-Order Waveplate, Multiple-Order Waveplate, Combinations of Multiple-Order Waveplates, Polymer Retarder, Mica Waveplate, Freshnel Rhomb, Achromatic, and Pseudo-Achromatic, etc.

For general information, it is noted that a Berek-type Compensator is a uniaxially anisotropic plate of material in which the Optical Axis is oriented perpendicularly to a plate surface thereof. When a Polarized Beam of Electromagnetic Radiation is caused to be incident other than along the Optical Axis, orthogonal components thereof encounter different effective Indicies of Refraction, thereby effecting retardation therebetween. A Zero-Order Quartz Waveplate is typically constructed by combining two Multi-Order (Quartz) Waveplates which have Optical Axes oriented at ninety (90) degrees with respect to one another. The two Multi-Order waveplates are selected so that the difference in retardation entered by each gives rise to an overall Zero-Order retardance characteristic. Polymer Compensators are made of a polymer material and can provide true Zero-Order retardance which, as do many Compensators, provides an inverse wavelength functional Retardation Characteristic. Essentially Achromatic (Pseudo-Achromatic) Compensators can be constructed by stacking appropriately chosen Polymer and Crystal waveplates. A potential advantage of said essentially Achromatic Compensators is that Retardance can be essentially constant over a range of wavelengths.

While it is known that generally available Compensators do not provide an exact Ninety (90) Degrees of Retardation at all wavelengths over a relatively large range of Wavelengths, the present invention, as described later herein, utilizes a Regression based Calibration procedure which compensates for said non-ideal Compensator Retardation characteristics. And while it is true that the sensitivity and accuracy of a Rotating Compensator System degrades as the Retardance provided by a utilized Compensator approaches zero (0.0) or one-hundred-eighty (180) degrees, it has been found that Compensators which demonstrate Retardation, over a range of utilized Wavelengths, of from forty (40) to one-hundred-seventy (170) degrees, are acceptable for use in the present invention, and allow achieving very impressive results over a demonstrated relatively large range of wavelengths, (eg. at least two-hundred-fifty (250) to one-thousand (1000) nanometers).

When the present invention Spectroscopic Rotating Compensator Ellipsometer System is used to investigate a Sample System present on said Stage for Supporting a Sample System, said Analyzer and Polarizer are maintained essentially fixed in position and at least one of said at least one Compensator(s) is/are caused to continuously rotate while a Polychromatic Beam of Electromagnetic Radiation produced by said Source of a Polychromatic Beam of Electromagnetic. Radiation is caused to pass through said Polarizer and said Compensator(s). Said Polychromatic Beam of Electromagnetic Radiation is also caused to interact with said Sample System, pass through said Analyzer, through a Converging Lens, become focused on an end of an Optical Fiber, exit a distal end of said Optical Fiber, and interact with said Dispersive Optics such that a Multiplicity of Essentially Single Wavelengths are caused to simultaneously enter a corresponding multiplicity of Detector Elements in said Detector System Photo Array.

While the present invention can utilize essentially any Compensator, a preferred embodiment of the present invention provides that at least one of said at least one compensator(s), which is mounted to rotate about the locus of a beam of electromagnetic radiation caused to pass therethrough, be selected from the group consisting of:

a single element compensator;

a compensator system comprised of at least two per se. zero-order waveplates, said per se. zero-order waveplates having their respective fast axes rotated to a position offset from zero or ninety degrees with respect to one another, with a nominal value being forty-five degrees;

a compensator system comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes and of the multiple order waveplates in said second effective zero-order wave plate being rotated to a position at a nominal forty-five degrees to the fast axes, respectively, of the multiple order waveplates in said first effective zero-order waveplate;

a compensator system comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes, respectively, of the multiple order waveplates in said first effective zero-order waveplate;

a compensator system comprised of at least one zero-order waveplate, and at least one effective zero-order waveplate, said effective zero-order wave plate, being comprised of two multiple order waveplates which are combined with the fast axes thereof oriented at a nominal ninety degrees to one another, the fast axes of the multiple order waveplates in said effective zero-order wave plate, being rotated to a position away from zero or ninety degrees with respect to the fast axis of the zero-order waveplate;

as are shown in FIGS. 5a-5e.

Additional compensator systems, as shown in FIGS. 5f-5m, which were previously disclosed in patent application Ser. No. 08/997,311, (now U.S. Pat. No. 5,946,098), and CIP's therefrom, and which are specifically within the scope of the invention and can be included in the selection group are:

a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said spectroscopic ellipsometer/polarimeter system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

A present invention spectroscopic rotatable compensator ellipsometer system can also comprise at least one compensator(s) which produces a retardance of, preferably, between seventy-five (75) and one-hundred-thirty (130) degrees over a range of wavelengths defined by a selection from the group consisting of:

a. between one-hundred-ninety (190) and seven-hundred-fifty (750) nanometers;

b. between two-hundred-forty-five (245) and nine-hundred (900) nanometers;

c. between three-hundred-eighty (380) and seventeen-hundred (1700) nanometers;

d. within a range of wavelengths defined by a maximum wavelength (MAXW) and a minimum wavelength (MINW) wherein the ratio of (MAXW)/(MINW) is at least one-and-eight-tenths (1.8).

Acceptable practice however, also provides for the case wherein at least one of said at least one compensator(s) provides a retardation vs. wavelength characteristic retardation between thirty (30.0) and less than one-hundred-thirty-five (135) degrees over a range of wavelengths specified from MINW to MAXW by a selection from the group consisting of:

a. MINW less than/equal to one-hundred-ninety (190) and MAXW greater than/equal to seventeen-hundred (1700);
b. MINW less than/equal to two-hundred-twenty (220) and MAXW greater than/equal to one-thousand (1000) nanometers;
c. within a range of wavelengths defined by a maximum wavelength (MAXW) and a minimum wavelength (MINW) range where (MAXW)/(MINW) is at least four- and one-half (4.5).

(NOTE, the specified vales and ranges can not be achieved by single plates with (1/wavelength) retardation characteristics).

The present invention will be better understood by reference to the Detailed Description Section of this Disclosure, in conjunction with the accompanying Drawings.

SUMMARY OF THE INVENTION

It is therefore a purpose and/or objective of the present invention to provide, in the context of a rotating compensator ellipsometer system, a converging lens and optical fiber combination such that after electromagnetic radiation is caused to interact with a sample, but before entering a detector, it is converged by said converging lens onto the end of an optical fiber.

It is another purpose and/or objective of the present invention to provide, in the context of a rotating compensator ellipsometer system, an optional spatial filter system and method for forming a beam of electromagnetic radiation which presents with an intensity profile which radially drops off quickly to zero (0.0) without demonstrating low level oscillations similar to Fourier Transform of a Square Wave characteristics.

It is another purpose and/or objective of the present invention to teach, either prior to or after a sample system, application of a conventional spatial filter system for forming a beam of electromagnetic radiation which, for instance, presents with an intensity profile which drops off quickly to zero (0.0), in spectroscopic rotating compensator ellipsometer systems.

Other purposes and/or objectives of the present invention will become obvious from a reading of the Specification and Claims.

BRIEF DESCRIPTION OF THE DRAWINGS

FIG. 1a1 shows a basic rotating compensator ellipsometer system as previously Patented in Parent U.S. Pat. No. 5,872,630.

FIG. 1a2 shows a general elemental configuration of an ellipsometer system indicating that a conventional Spatial Filter (SF) can be present, said system including a present invention Converging Lens (L) and Optical Fiber (F).

FIG. 1a3 shows another general elemental configuration of an ellipsometer system indicating that a conventional Spatial Filter (SF) can be present, said system including a present invention Converging Lens (L) focused on an Aperture (AP), which can comprise an Optical Fiber present therewithin.

FIGS. 1a4 and 1a5 show that at least one conventional Spatial Filter (SF) can be present at least one location somewhere in the demonstrate Rotating Compensator Ellipsometer System, and that a Lens (L) Optical Fiber (F) is present prior to a dispersive optic (DO).

FIG. 1a6 shows the system of FIG. 1a with the Converging Lens (L) and Optical Fiber (F) of the present invention added.

FIG. 1a7 shows the components of a Reflectance Mode Material System Investigation Systems which has five apertures in the pathway of an electromagnetic beam prior to a material system, and four thereafter.

FIG. 2 shows an example of a source of electromagnetic radiation comprising a light fiber, lens, apertures and polarizer.

FIG. 4 shows the effect of the presence of a spatial filter on the radial intensity of an electromagnetic beam as is developed and utilized in spectroscopic rotating compensator ellipsometers.

FIGS. 5a-5m show various Compensator designs which can be applied in the present invention spectroscopic rotating compensator ellipsometers.

DETAILED DESCRIPTION

Turning now to the Drawings, there is shown in FIG. 1a1 a basic Rotating Compensator Ellipsometer system as disclosed in Parent U.S. Pat. No. 5,872,630, demonstrating both reflection and transmission modes, and comprising a Source of Electromagnetic Radiation (LS), a Polarizer (P), Compensator(s) (C) (C') (C"), and a Detector (DET). Source (LS) is shown to provide a beam of electromagnetic radiation (PPCLB), and a beam of electromagnetic radiation (EPCLB) is shown reflecting from/transmitting through a Sample System (SS). FIG. 1a6 shows the system of FIG. 1a1 with the distinguishing Converging Lens (L) and Optical Fiber (F) of the present invention added. The effect of the Converging Lens (L) and Optical Fiber (F) is to eliminate an outer annulus of a beam focused on an end of the Optical Fiber (F), by said Converging lens as demonstrated by FIG. 4 herein.

Figure 2:
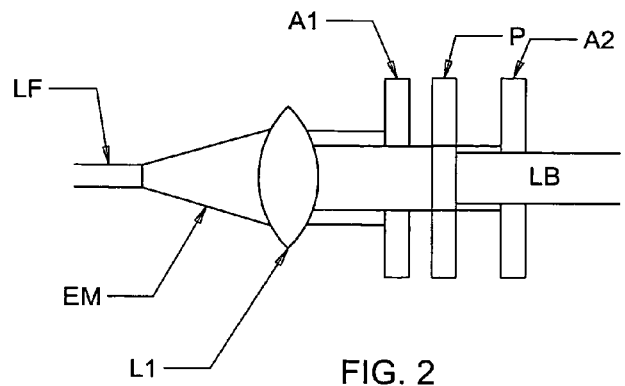

FIG. 1a2 shows a general elemental configuration of an ellipsometer system to which the present invention can be applied to investigate a sample system (SS). Shown for reflection and transmission are:

a. a Source of a beam electromagnetic radiation (LS);
b. a Polarizer (P);
c. a Compensator (C1);
d. optional additional element(s) (AC1);
e. a sample system (SS);
f. optional additional element(s) (AC2);
g. a Compensator (C2);
h. an Analyzer (A);
i. a Converging Lens (L);
j. an Optical Fiber (F); and
i. a Detector System (DET).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. optional "additional elements", (AC1) and (AC2), can be considered as being, for instance, optional input and output lenses or perhaps windows in a vacuum chamber. Also note that after the Polarizer (P) there is indicated, in dashed lines, the presence of an optional conventional Spatial Filter (SF). As better demonstrated in FIGS. 1a4 and 1a5, other optional conventional Spatial Filter (SF) locations in a rotating compensator ellipsometer system, such as prior to the Polarizer (P), after the Compensator (C1) or after the Additional Elements (AC1), or on the Detector (DET) side of the Sample System (SS), before or after the additional element(s), (AC2); Compensator (C2); and Analyzer (A), are included in the scope of the present invention. FIG. 1a2 is distinguished by the Converging Lens (L) and Optical Fiber (F).

Another embodiment of an ellipsometer system to which the present invention can be applied is shown in FIG. 1a3, which shows a Perspective view of a demonstrative system. FIG. 1a3 shows a Light Source (LS) and a Polarizer (P), which in combination serve to produce a generally horizontally oriented Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become generally vertically oriented Polarized Beam of Electromagnetic Radiation (LBI'), then interact with a Sample System (SS) present on a Sample System supporting Stage (STG). FIG. 1a3 shows that said interaction with the Surface (S) of said Sample System (SS) causes a generally vertically oriented Polarized Beam of Electromagnetic Radiation (LBO') to pass through Focusing Optic (F2). FIG. 1a3 show that after passing through Focusing Optic (F2) said generally vertically oriented Polarized Beam of Electromagnetic Radiation (LBO') interacts with Optical Element, (eg. Prism), (PRO) and is essentially totally internally reflected thereby to become generally horizontally oriented Polarized Beam of Electromagnetic Radiation (LBO), which generally horizontally oriented Polarized Beam of Electromagnetic Radiation (LBO) passes through Analyzer (A) and then enters Detector System (DET), via Circular Aperture (AP), for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Sample System (SS). The Re-Collimated generally vertically oriented Beam of Electromagnetic Radiation (LBI') being identified as generally horizontally oriented Beam of Electromagnetic Radiation (LBO) after it has been caused to interact with Prism (PRO).

Also, as in the FIG. 1a2 case, note that after the Polarizer (P) there is indicated, in dashed lines, the presence of an optional conventional Spatial Filter (SF). Shown are a Pin Hole (PH), (which electromagnetic beam (LB1) passes through), which Pin Hole (PH) is located in a Diaphram which is located at essentially a Focal Length distant from each of Lenses (SFL1) and (SFL2). Again, while other pre-sample system locations are included in the scope of the invention, the shown location is preferred for systems that include such a conventional Spatial Filter. Note that either of said Lenses (SFL1) and (SFL2) can be replaced with a functionally essentially equivalent mirror. FIG. 1a2 is distinguished by the Converging Lens (L) and Aperture (AP), which can comprise an Optical Fiber (F) therewithin.

Figure 4:
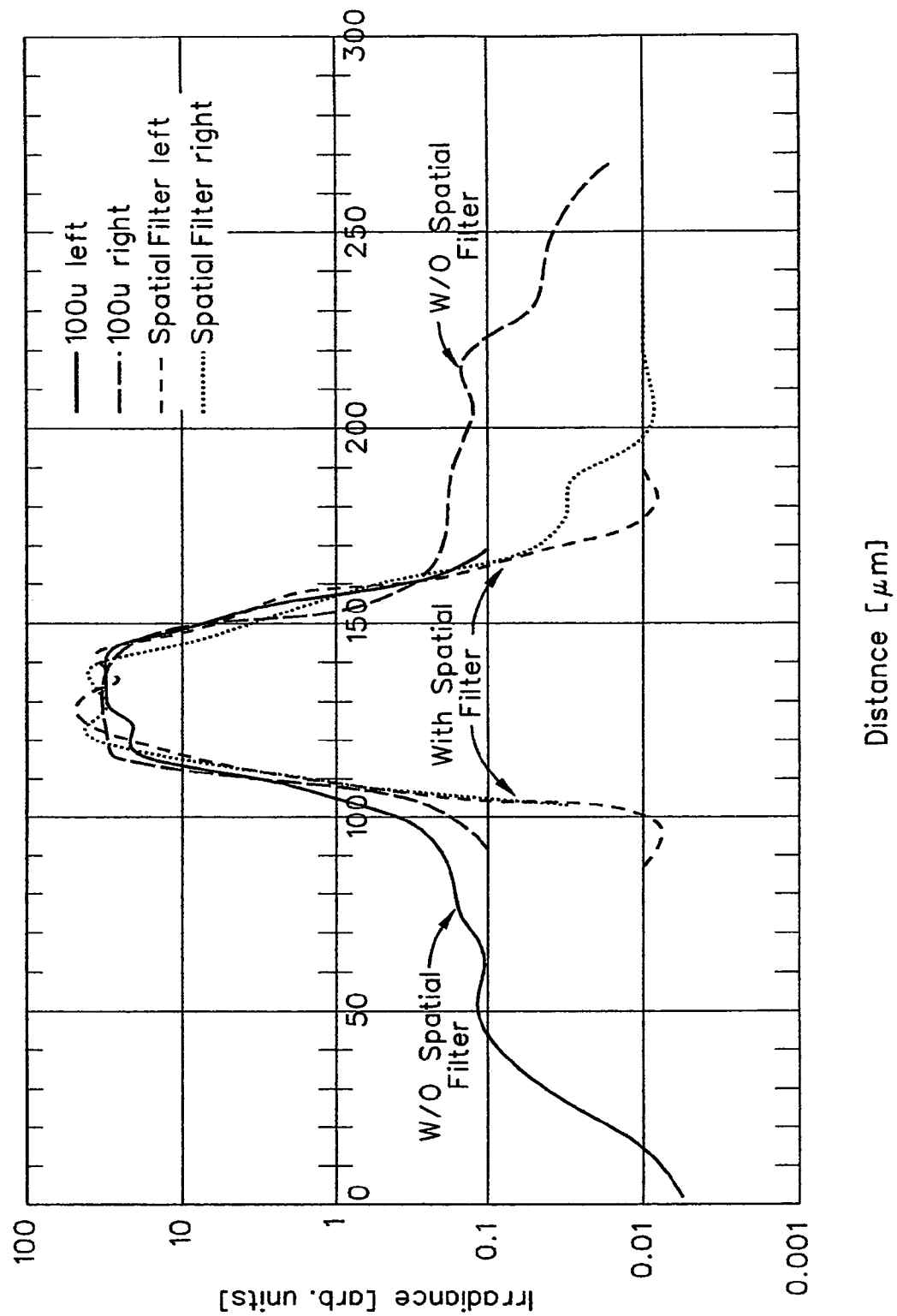

FIG. 1a4 shows a Spectroscopic Reflectance Mode version of the Rotating Compensator Ellipsometer System shown in FIG. 1a1, with the Detector Elements (DE's) containing Photo Array Detector System (DET) shown present directly after the Analyzer (A). FIG. 1a4 is distinguished by the Converging Lens (L) and Optical Fiber (F).

FIG. 1a5 shows another present invention system Reflectance Mode Rotating Compensator Ellipsometer System System configuration in which three (3)-Detectors (Det 1), (Det 2) and (Det 3) are fed input by Fiber Optics (LF1), (LF2) and (LF3) present in a Fiber Optic Bundle exiting Fiber Optic Connector (LFC). Said Fiber Optic Connector (LFC) receives a Polarized Electromagnetic Beam (EPCLB) exiting the Analyzer (A). Said three (3) Detectors (Det 1), (Det 2) and (Det 3) can be previously disclosed Off-the-shelf Zeiss Diode Array Spectrometers, and can each comprise a Focusing Element (FE) in functional combination with a Dispersive Optics (DO) and a Diode Element (DE) containing Photo Array (PA). (Zeiss Diode Array Spectrometers provide, for instance, operational wavelength ranges selected from the group consisting of: (300-1150 nm, 190-230 nm, 190-400 nm and 900-2400 nm). It is also mentioned that diffraction grating (DO) can be selected from the group consisting of: (a "lined", a "blazed", and a "holographic" geometry), said lined geometry consisting essentially of symmetrical alternating lines with depressions therebetween, and said blazed geometry consisting of alternating ramp shaped lines with depressions therebetween, and said holographic geometry consisting of continuous cosine shaped lines and depressions), all of which are known in the literature.

Both FIGS. 1a4 and 1a5 show that optional conventional Spatial Filters (SF) can present at least one location somewhere in the demonstrate Rotating Compensator Ellipsometer System. It is emphasised that said at least one Spatial Filter Equivalent (SF) can be placed anywhere in the present invention Spectroscopic Rotating Compensator Ellipsometer System, including the shown preferred location just prior to the Dispersive Optics (DO). FIG. 1a4 is distinguished by the Converging Lens (L) and Optical Fiber (F) prior to the Fiber Optic Connector (LFC) which accepts a single input Optical Fibers and provides a plurality thereof as output.

It is also noted that Fiber Optics can be utilized to carry Polychromatic Electromagnetic Radiation from a Source thereof (LS) to the position of a Polarizer (P), or from the position of an Analyzer (A) to a Detector (DET) in FIGS. 1a1-1a4, (see for instance (LF1), (LF2), and (LF3)).

Analogically similar figures to those shown in FIGS. 1a3-1a5, but oriented for use in a Transmission Mode are not shown, but should be understood as within the scope of the present invention as implied by FIG. 1a1. Again, the present invention version of such systems are distinguished by the presence of a Converging Lens (L) and Optical Fiber (F).

FIG. 1a7 shows the components of a Reflectance Mode Material System Investigation Systems which has five apertures in the pathway of an electromagnetic beam prior to a material system, and four thereafter. For insight, FIG. 1a7 is included to show a preferred polychromatic rotating compensator material system investigation system comprising a source (LS) of polychromatic beam (14) of electromagnetic radiation, a first aperture (A1), a second aperture (A2), a fixed polarizer (P), a rotating compensator (C), a third aperture (A3), a forth aperture (A4), a first substantially achromatic lens (AL1), a fifth aperture (A5), a stage (STG) for supporting a material system, a sixth aperture (AG), a second substantially achromatic lens (AL2), a seventh aperture (A7), an eighth aperture (A8), a fixed analyzer (A), a ninth aperture (A9), a third substantially achromatic lens (AL3), an optical fiber (OF) and a detector means (DET) which contains a dispersive element and a multiplicity of detector means elements, there further being a UV filter (F1) present between said source (LS) of polychromatic beam of electromagnetic radiation and said stage (STG) for supporting a material system. When said polychromatic rotating compensator material system investigation system is used to investigate a material system (MS) present on said stage (STG) for supporting a material system, said fixed analyzer (A) and fixed polarizer (P) are maintained essentially fixed in position and said rotating compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantially achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantially achromatic lens (AL2), seventh aperture (A7), eighth aperture (A8), fixed analyzer (A), ninth aperture (A9), third substantially achromatic converging lens (L), enter said Optical Fiber (F) and therevia enter said detector means (DET). It is the combination of the Converging Lens (L) and Optical Fiber (F) that distinguishes the present invention.

It is also mentioned that in the following it will be generally assumed that a Material System (MS) under investigation by a Spectroscopic Rotating Compensator Ellipsometer System is positioned upon the Material System Supporting Stage (STG). This need not be the case, as is described in U.S. Pat. No. 5,706,087 wherein a Material System (Sample), (MS) can be positioned in a Magneto-Optic System which is physically too large to be supported by said Material System Supporting Stage (STG), or in an environmental control chamber. Further, especially where Ultraviolet range wavelengths are utilized, the system can be placed into an evacuated or purged, (eg. by nitrogen or argon), Chamber to the end that UV absorbing Oxygen and Water Vapor are not present therewithin. The entire system can be so encompassed within a said Chamber, or only the Sample (MS) Stage portion thereof. The Chamber, where utilized, can be of multiple region construction.

FIG. 2 shows that a Light Source (LS) can comprise a Light Fiber, a Lens (L1), and a First Aperture (A1). In the context of an ellipsometer a Polarizer (P) is also shown as it would be positioned. Shown in addition is a second Aperture (A2). In use electromagnetic radiation (EM) exiting the Light Fiber (LF) expands and enters Lens (L1) and is collimated thereby. First Aperture (A1) limits the beam diameter, and Second Aperture (A2) further does so to provide a beam of electromagnetic radiation labeled (LB). The important present invention aspect shown in FIG. 2 is that the beam (LB) entering the Converging Lens (L) is focused onto the end of the Optical Fiber (F), but an outer Annualar (ANU) region of the converged beam does not enter the Optical Fiber (F).

As originally disclosed in Allowed Parent application Ser. No. 10/178,723, FIG. 3a expands on FIG. 2. The presence of a Sample (SS) is implied, and thereafter is shown a present invention Converging Lens (L) and Optical Fiber (F) positioned to receive focused electromagentic radiation (LB) after interaction with said Sample (SS). Note that the outer annulus of the electromagentic radiation (LB) after interaction with said Sample (SS) does not enter said Optical Fiber (F).

Figure 3A:
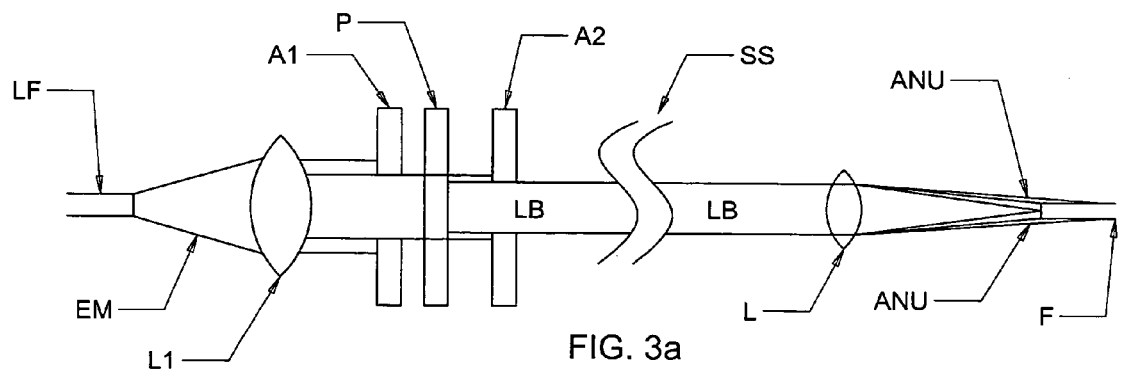
FIG. 3a shows an example of a present invention Converging Lens (L) and Optical Fiber (F) in combination with the system of FIG. 2.
Figure 3B:
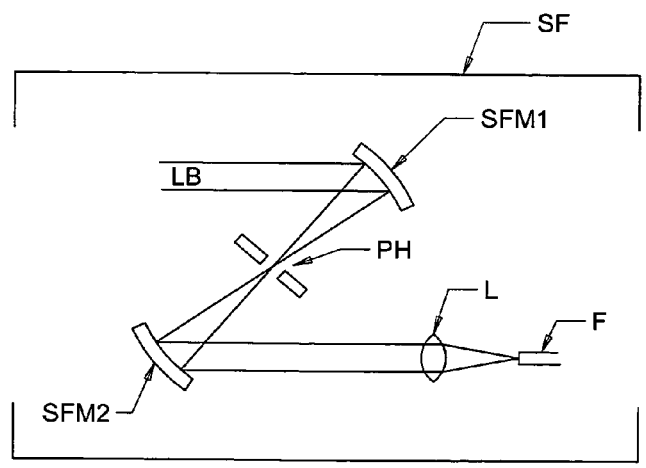
FIG. 3b shows alternative spatial filter construction which can be applied in the context of a FIG. 2 system, including the present invention Converging Lens (t) and optical Fiber (F).

FIG. 3b shows alternative conventional Spatial Filter (SF) construction in which mirrors (SFM1) and (SFM2) perform the function of lenses (SFL1) and (SFL2) in FIG. 3a. That is the conventional Spatial Filter shown in FIG. 3a can be replaced with that in FIG. 3b. It is further noted that a conventional Spatial Filter could comprise one Lens and one Mirror, in either order in a conventional Spatial Filter, hence the language "lens or mirror" is to be interpreted broadly as meaning that each is independently selected from the group consisting of a lens and a mirror. Again, the present invention Converging Lens (L) and Optical Fiber (F) are shown, and distinguish the present invention.

FIG. 4 shows the effect of the presence of the conventional Spatial Filter (SF) as shown in FIG. 3a on the Intensity Profile of a beam of electromagnetic radiation passed therethrough. Note that FIG. 4 plots Intensity on a Log Axis, and that the Intensity drops toward 0.001 much quicker when the conventional Spatial Filter is in place than when it is not in place. The present invention combination of a Converging Lens (L) and Optical Fiber (F) provides a similar result.

The present invention also includes, in the context of a spectroscopic rotating compensator ellipsometer and the like systems, the method of removing an radial outer annular ring from an electromagnetic beam by use of an equivalent to a spatial filter. Said method can be recited as a method of processing source electromagnetic radiation beams to eliminate a radially outer annulus thereof, said outer annulus being comprised of low intensity level irregular content, said method comprising placing at least one spatial filter(s) such that said electromagnetic beam passes therethrough. The present invention accomplished said result by the combination of a Converging Lens (L) and Optical Fiber (F).

The terminology "outer annular region" as used herein is to be interpreted to mean an outer region of an electromagnetic beam, as distinct from a central region thereof, which outer region appears as an annulus when it is considered that the intensity of the beam decreases to zero as the radius increases to infinity. Said "outer annulus region" at times begins at the point where the intensity of an electromagnetic beam falls to approximately ten (10%) percent of its maximum intensity, and it is noted, might contain approximately two (2%) to five (5%) of the electromagnetic beam's energy content.

It is also noted that a present invention Compensator (C) (C'), (C") is typically an Off-the-Shelf Quarter-Wave-Plate with its Optical Axis in the plane of a surface thereof, or Berek-type with its Optical Axis perpendicular to a surface thereof, and is selected without special concern to its Achromatic Operating Characteristics, emphasis added. Note that a Zero-Order Waveplate can be constructed from two (2) Multiple-Order Waveplates of different thicknesses (T1) and (T2) which have Optical Axes oreinted Ninety (90) degrees to one another, such that the overall effect of retardation in in the Zero-Order. As well, said Compensator (C), (C'), (C") can be made of essentially any functional material such as Quartz or Polymer etc.

Now, and importantly, even though the Present Invention Rotating Rotating Ellipsometer System is Spectroscopic, (ie. simultaneously operates on a number of Wavelengths in a Beam containing many Electromagnetic Wavelengths, over a range of, for instance, 190-1000 nanometers), a Compensator (C), (C'), (C") utilized therein can provide a Retardance which, for instance, varies inversely with Wavelength and still be usable. A Compensator (C), (C'), (C") does however, typically, have to be of a nature to allow passage of a Polychromatic Electromagnetic Beam therethrough without causing significant Attenuation, Deviation or Displacement in the Direction of Propagation thereof. If this is not the case, difficult to compensate complexities are caused in Detector Elements (DE's) containing Photo Array Detector System (DET) Detector Element Output Signals.

The reason the Present Invention can operate with a Compensator (C), (C'), (C") that does not provide even close to a Constant Ninety (90) Degree Retardance over a range of Wavelengths, (which would constitute Ideal Characteristics), is that a Regression based Calibration Procedure utilized, (see U.S. Pat. No. 5,872,630 which is incorporated by reference hereinto, and which is co-owned with this application), provides Wavelength dependent Compensation effecting values for Calibration Parameters as required in a developed Mathematical Model of the present invention Rotating Compensator Ellipsometer System. As better described in the 630 patent the Inventors develop a Calibration Parameter Containing Mathematical Model of the present invention Rotating Compensator Ellipsometer System by, for instance, utilizing Matrix Representations for various System Components involved, then multiplies out the Matrices in an appropriate order to provide a Transfer Function. This applies for all Wavelengths monitored by a Detector Elements (DE's) containing Photo Array Detector System (DET) Detector Element (DE). Next, Data Set(s) are Experimentally obtained as a function of wavelength and typically as a function of various settings of the Polarizer (P) or Analyzer (A), (or both could be rotated to various positions), while a Compensator (C) rotates at, typically though not necessarily, Twenty (20) to Thirty (30) Hz. Other rotation speeds can be utilized and if two Compensators are present one or both can be caused to rotate, and if both are caused to rotate, as mentioned earlier herein, they can be caused to rotate at the same, or different, speeds. (Note that Data Set(s) could also be achieved utilizing variation of Angle-Of-Incidence of a Beam of Polychromatic Radiation with respect to a Sample System under investigation). Calibration Parameters in the Mathematical Model are then evaluated by, typically, Mean-Square-Error based Regression onto the Data Set(s). It is also possible to effectively find Calibration Parameter containing Mathematical Expressions for Coefficients of Mathematical Series, (eg. Fourier Series), which comprise the Mathematical Model Transfer Function, and calculate Numerical Values for the Coefficients from the Data Set(s), then effectively perform Regression of said Calibration Parameter containing Mathematical Expressions for Coefficients of Mathematical Series Transfer Function onto said Numerical Values for the Coefficients from the Data Set(s). It is emphasized that a single Two-Dimensional Data Set has been found sufficient to allow excellent Calibration results to be achieved. Said Two-Dimensional Data Set typically is Intensity vs. Wavelength, and Polarizer or Analyzer Azimuthal Rotation Angle settings. In addition, said Two-Dimensional Data Set can be obtained from a present invention Rotating Compensator Ellipsometer System oriented so that a Polychromatic Beam of Electromagnetic Radiation interacts with a Sample System or such that said Polychromatic Beam of Electromagnetic Radiation passes through the present invention Rotating Compensator Sample System Investigation System without interacting with a Sample System, other than a Sample System comprised of "Open Atmosphere". The present invention Rotating Rotating Ellipsometer System can also, of course, be Calibrated utilizing more than one Data Set as well, but as alluded to, this has not been found necessary. This is mentioned as the invention reported in Co-pending patent application Ser. No. 08/618,820, wherein a Rotating Rotating Ellipsometer System utilized in the Infra-red band of wavelengths, requires that two (2) Data Sets be present, (eg. selected with the Rotating Compensator Sample System Investigation System oriented in a manner selected from the group: ("Straight-Through", "Sample Sample Present", "Alternative Sample Sample Present")). Both Data Sets are simultaneously utilized in a Regression Procedure to evaluate numerous Calibration Coefficients in a Mathematical Model which is described in the Ser. No. 08/618,820 application. The reason that only one (1) Data Set is required to practice the described present invention Calibration Procedure, is that the number of Calibration Parameters required by the Mathematical Model of the present invention, (which is not operated in the Infra-red range of wavelengths), is much fewer that the number of Calibration Parameters required by the Mathematical Model of the Rotating Rotating Ellipsometer System operated in the Infra-red range of wavelengths. The present invention Rotating Compensator System Mathematical Model typically involves as few as Five (5) Calibration Parameters, (where only one Compensator is present), in combination with simultaneous determination of a Sample System PSI and DELTA. (It is noted that a straight-through mode essentially provides open atmosphere as a Sample System and that the PSI and DELTA of open atmosphere are forty-five (45) degrees and zero (0.0) degrees, respectively). Said Five (5) Calibration Parameters are Azimuthal Orientation Angles for Polarizer (Ps), Analyzer (As), Compensator (Cs), and Compensator Retardance Parameters (P0) and (P1). Equations (45) and (46) serve as further demonstratration of this point. (Note that the (Ps), (Cs) and (As) Azimuthal Orientation Calibration Angles can be thought of as serving to align the Polarizer, Compensator and Analyzer Azimuths with a Sample System Frame of Reference). Of course, if two Compensators are present then an additional Compensator Orientation Angle (Cs2) and Compensator Retardance Parameters (P0') and (P1') and additional would also have to be evaluated. (It is noted that Retardation entered between orthogonal components of a Polarized Electromagnetic Beam, by a Compensator, is accounted for by a Matrix Component, and typically the r4 term of a Jones Matrix, but such is accounted for by Compensator Retardance Parameters (P0), (P1), (P0'), (P1') in the presently described Calibration Procedure).

Continuing, the present invention achieves a Spectroscopic Rotating Rotating Ellipsometer System preferably utilizing an "Off-The-Shelf" compact Spectrometer Systems, and utilizing "Off-The-Shelf" Compensator Components which are not at all "ideal", as regards Achromaticity. To put this into perspective, it is noted that to date, there is no known Spectroscopic Rotating Compensator Ellipsometer available in the market-place. It is believed that this is because it has previously been believed that to achieve such a System an Achromatic Rotating Compensator (RC) would be required. Such Compensators are not generally commercially available, hence, are expensive and reasonable approximations thereof typically must be individually fabricated. (Note, as described in patent application Ser. No. 08/618,820, (now U.S. Pat. No. 5,706,212), a Dual-Rhomb Rotating Compensator (RC) which provides about seven (7%) percent variation in Retardation effected over a range of Wavelengths of approximately 2 to 14 microns, has been developed at the University of Nebraska. However, it is not clear that even the identified University of Nebraska Dual-Rohmb Rotating Compensator (RC) would operate "Achromatically" outside the identified range of wavelengths).

Further, essentially any Compensator which can be placed into a beam of electromagnetic radiation can be applied, such as those disclosed in claim 9 of U.S. Pat. No. 5,872,630, (which 630 patent is incorporated by reference hereinto):
  Berek-type;
  Non-Berek-type;
  Zero Order;
  Zero Order comprising a plurality of plates;

Rhomb;
Polymer;
Achromatic Crystal; and
Psuedo-Achromatic.

Figure 5A:
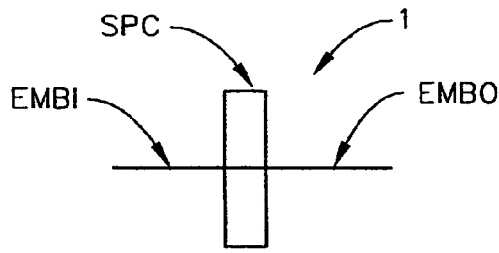
Figure 5B:
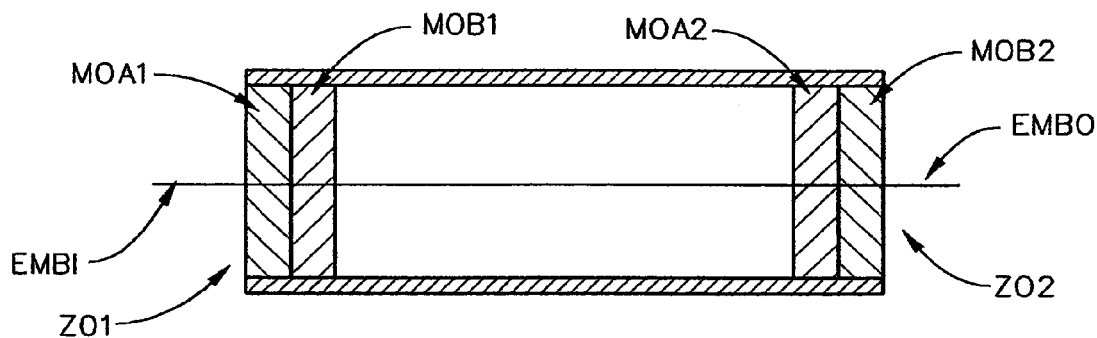
Figure 5C:
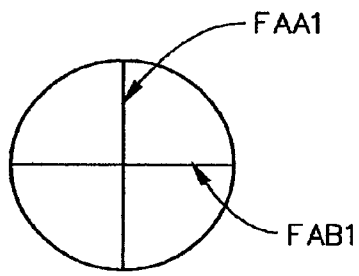
Figure 5D:
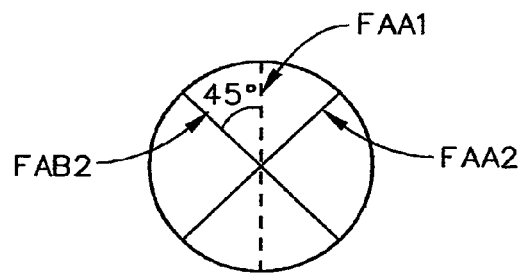
Figure 5E:
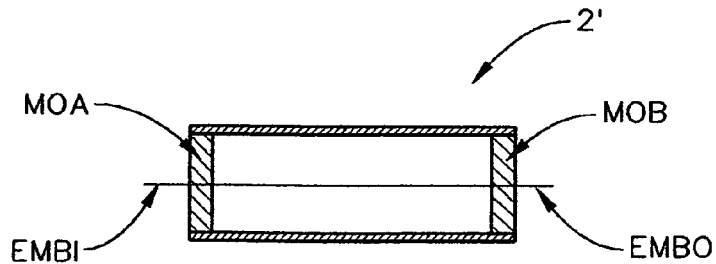

FIGS. 5a, 5b, 5c, 5d and 5e demonstrate functional construction of preferred present invention compensator systems. FIG. 5a simply exemplifies that a single plate (SPC) compensator (1) can be applied. FIG. 5b demonstrates construction of a compensator (2) from first (ZO1) and second (ZO2) effectively Zero-Order, (eg. Quartz or Bicrystalline Cadnium Sulfide or Bicrystalline Cadnium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 5b is a cross-sectional side view of a present invention preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength. FIGS. 5c and 5d are views looking into the left and right ends of the preferred present invention Compensator (PC) as shown in FIG. 5b, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (ZO1). (Note that the fast axis (FAA1) of the first effective Zero-Order Waveplate (ZO1) is shown as a dashed line in FIG. 5d, for reference). FIG. 5e demonstrates functional construction of another preferred compensator (2') which is constructed from two per se. single plate Zero-Order Waveplates (MOA) and (MOB), which are typically made of materials such as mica or polymer. (It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 5f-5m demonstrate additional compensators which can be applied in the present invention.

Figure 5F:
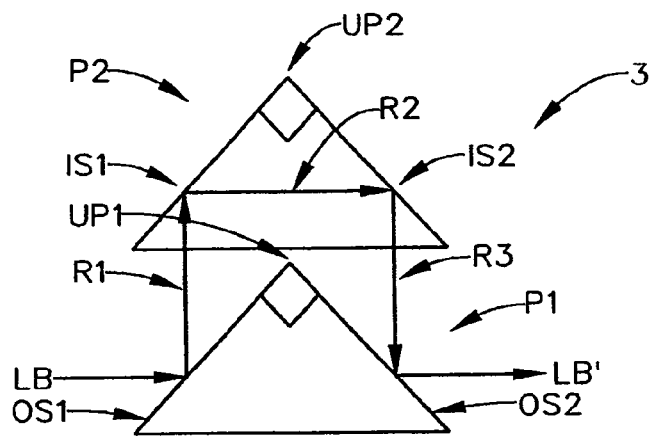

FIG. 5f shows that the first additional present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 5f, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational misalignments of the input light beam (LB). As well, the total retardance provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

Figure 5G:
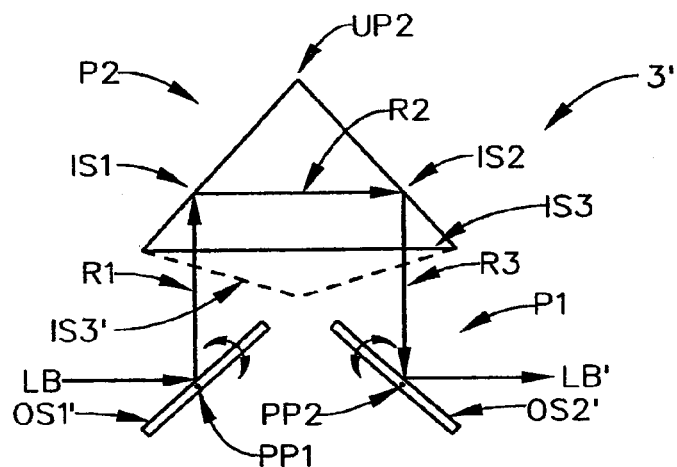

FIG. 5g shows a variation (3') on FIG. 5f, wherein the first triangular shaped element is replaced by two rotatable reflecting means, identified as (OS1') and (OS2'). This modification allows user adjustment so that the locus of an entering electromagnetic beam (LB') exits undeviated and undisplaced from an entering electromagnetic beam (LB).

Figure 5H:
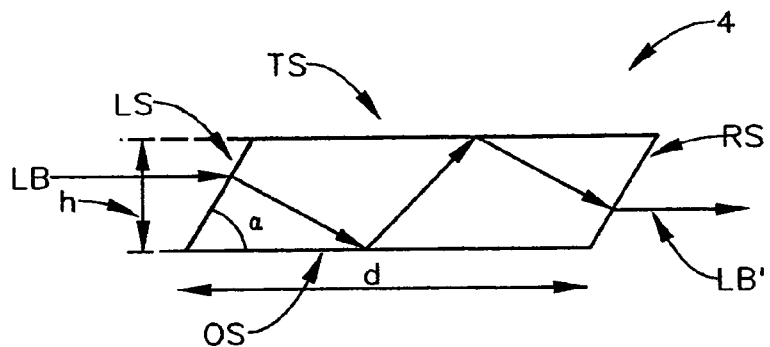
Figure 5I:
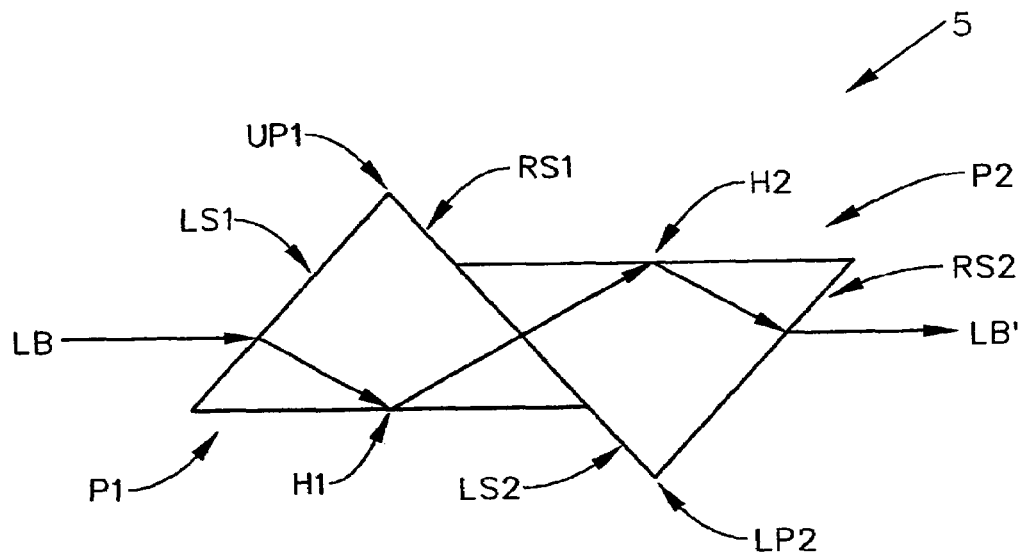

FIG. 5h shows that the second additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos( )), where alpha ( ) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha ($\propto$) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

FIG. 5i shows that the third additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that the triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 5J:
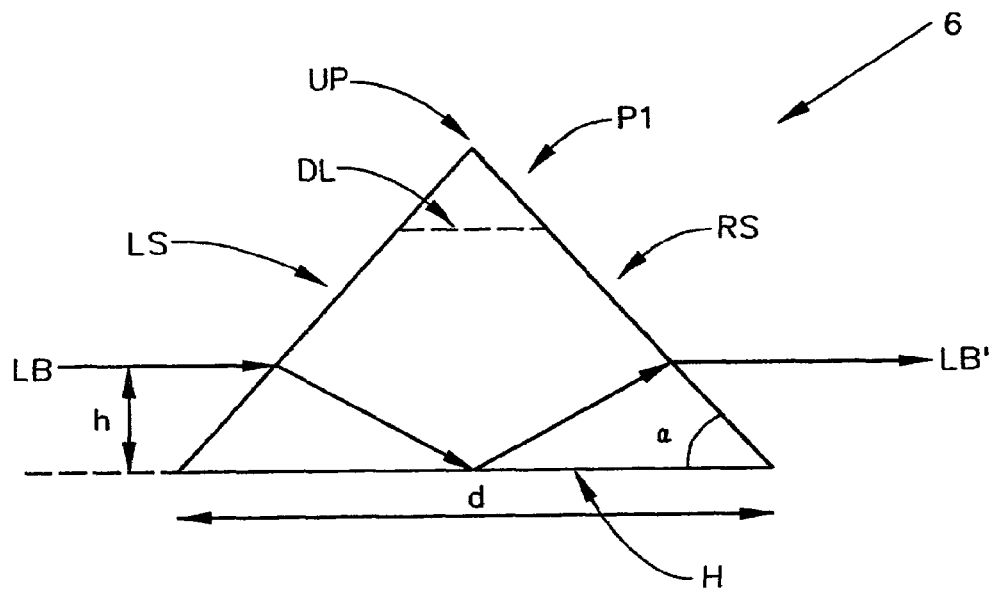

FIG. 5j shows that the forth additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 5i retarder system (6) is typically an isosceles prism which is available off-the-shelf with an angle alpha ( ) of forty-five (45) degrees. As long as the input electromagnetic beam (LB) height (h) is chosen in accordance with the formula:

in conjunction with the index of refraction (n) of the material from which the FIG. 5j retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

FIG. 5m shows that the fifth additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2)

and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

FIG. 5k1 shows that the sixth additional present invention retarder system (8) comprises first (BK1) and second (BK2) Berek-type retarders which each have an optical axes essentially perpendicular to a surface thereof. As shown by FIG. 5k2, each of said first (BK1) and second (BK2) Berek-type retarders can have fast axis which are oriented other than parallel to one another, but for the presently described retarder system it is assumed that the fast axes are aligned, (ie. an angle PHI ($\phi$) of zero (0.0) degrees exists between fast axes of the two Berek-type (BK1) and (BK2) plates in FIG. 5k1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardance introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately half of achieved retardance. This insensitivity results because if the input electromagnetic beam is slightly changed, one of said plates will contribute slightly more (less), but the second slightly less (more) retardance because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardance characteristic which, without more, makes use over a wide spectral range difficult.

A variation of the just described retarder system (8) applies to the seventh additional present invention retarder system (9) as well, with the difference being that a FIG. 5k2 offset angle PHI ($\phi$) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 5l1 serves as the pictorial reference for the eighth additional present invention retarder system (8) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 5l2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

A ninth present invention retarder system (9) is also pictorially represented by FIG. 5/1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different. FIG. 5/2 shows the relative angular orientations between pairs of Berek Plates.

It is also to be appreciated that no other Spectroscopic Rotating Compensator System is known which comprises at once:
1. at least one non-Achromatic Characteristic Rotating Compensator (RC);
2. a Dispersive Optics (DO);
3. a Detector Elements (DE's) containing Detector System (DET) which comprises a Photo Array (PA); such that in use a Multiplicity of Sample System (SS) Investigation Wavelengths in a Polychromatic Beam of Electromagnetic Wavelengths are simultaneously Monitored; and
4. a Converging Lens (L) and Optical Fiber (F) located prior to a Detector (DET).

It is emphasized that the present invention is considered to be particularly impressive as it is relatively easily constructed utilizing commercially available "Off-The-Shelf" Diode Array Spectrometer Systems, and non-ideal Compensators. The present invention conveniently provides, in a commercially realizable format, that which was thought to be, prior to the present invention, essentially impossibly to provide in other than a prohibitively expensive, (and perhaps difficult to calibrate and utilize), single unit format.

It is to be understood that a Photo Array can be comprised of Diode-Elements, Charge-Coupled-Devices, Bucket-Brigade-Devices and equivalents.

It is noted that "deviation" refers to a change in the direction, and displacement refers to an offset in said direction of propagation of propagation of a beam of electromagnetic radiation, when it passes through an optical element.

It is also noted that Polychromatic Electromagnetic Beam Source can be comprised of a combined plurality/multiplicity of Laser Sources, and that Polychromatic Electromagnetic Beam Source can include an effective Polarizer therewithin, thereby eliminating the need for a separate Polarizer. Such cases are to be considered within the scope of the Claims.

It is also noted that the language "at least partially pass there-through" regarding an electromagnetic beam interaction with a pin hole in a diaphram, means that at least a part of said beam passes through the aperture, said part typically being centrally located in said beam, with an annular region being blocked passage.

Finally, it is to be understood that a conventional spatial filter basically sequentially consists of beam converging at least one lens and/or mirror, a diaphram with a pin hole therein located essentially at the focal length of said beam converging lens and/or mirror, and a second beam collimating at least one lens and/or mirror. However, it should be appreciated that, for instance, a first beam collimating lens and aperture can be added and the resulting system still be within the scope of a conventional spatial filter.

The present invention is distinguished by a sequence of a Converging Lens (L) and an Optical Fiber position after a sample in the contest of a Rotating Compensator Ellipsometer or the like system.

Having hereby disclosed the subject matter of this invention, it should be obvious that many modifications, substitutions and variations of the present invention are possible in light of the teachings. It is therefore to be understood that the present invention can be practiced other than as specifically described, and should be limited in breadth and scope only by the Claims.

We claim:

1. A spectroscopic rotating compensator ellipsometer system comprising a source of a polychromatic beam of electromagnetic radiation, a polarizer, a stage for supporting a sample system, an analyzer, a dispersive optics and at least one detector system which contains a multiplicity of detector elements, said spectroscopic rotating compensator ellipsometer system further comprising at least one compensator(s) positioned at location(s) selected from the group consisting of:

before said stage for supporting a sample system; and
after said stage for supporting a sample system; and
both before and after said stage for supporting a sample system;

such that when said spectroscopic rotating compensator ellipsometer system is used to investigate a sample system present on said stage for supporting a sample system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said sample system, pass through said analyzer and interact with said dispersive optics such that a multiplicity of essentially single wavelengths are caused to simultaneously enter a corresponding multiplicity of detector elements in said at least one detector system;

the improvement being that said spectroscopic rotating compensator ellipsometer system further comprises, after a sample system:

at least one spatial filter equivalent comprising a focusing lens and an optical fiber oriented such that electromagnetic radiation focused by said focusing lens enters an end of said optical fiber, said spatial filter equivalent serving to attenuate an outer annular region from said electromagnetic beam as it passes therethrough.

2. A system as in claim 1 in which further comprises a conventional spatial filter that sequentially comprises:
- first beam collimating single or multiple element lens;
- aperture;
- beam converging at least one lens and/or mirror;
- diaphram with a pin hole therein located essentially at the focal length of said at least one beam converging lens and/or mirror; and
- second beam collimating at least one lens and/or mirror;

such that in use the central portion of the electromagnetic beam which is collimated by said first beam collimating single or multiple element lens is caused to pass through said aperture, become focused on and at least partially pass through said pin hole in said diaphram by said at least one beam converging lens and/or mirror, and become recollimated by said second beam collimating at least one lens and/or mirror.

3. A system as in claim 1 which further comprises, after said source of polychromatic beam of electromagnetic radiation a conventional spatial filter which sequentially comprises:
- beam converging at least one lens and/or mirror;
- diaphram with a pin hole therein located essentially at the focal length of said at least one beam converging lens and/or mirror; and
- beam collimating at least one lens and/or mirror;

such that in use an electromagnetic beam of radiation is caused to become focused on and at least partially pass through said pin hole in said diaphram by said beam converging at least one lens and/or mirror, and then become recollimated by said beam collimating at least one lens and/or mirror.

4. A system as in claim 1, in which the spectroscopic rotating compensator ellipsometer system is characterized as:
- a polarization state generator comprising said source of a polychromatic beam of electromagnetic radiation and said polarizer prior to said means for supporting a sample system; and
- a polarization state detector comprising said analyzer, a dispersive optics and at least one detector system which contains a multiplicity of detector elements, after said means for supporting a sample system;

at least one of said polarization state generator and polarization state detector further comprising a compensator;
a conventional spatial filter being present in at least one selection from the group consisting of:
- said polarization state generator; and
- said polarization state detector.

5. A system as in claim 4, in which said at least one conventional spatial filter sequentially comprises:
- first at least one lens and/or mirror;
- pin hole containing diaphram; and
- second at least one lens and/or mirror;

said pin hole containing diaphram being positioned near the focal points of said first and second at least one lenses and/or mirrors, such that a collimated electromagnetic beam enters said first at least one lens and/or mirror, is converged and at least partially passes through said pin hole, and is re-collimated by said second at least one lens and/or mirror.

6. A system as in claim 1, which further comprises at least one conventional spatial filter between said analyzer and polarizer which sequentially comprises:
- first at least one lens and/or mirror;
- pin hole containing diaphram; and
- second at least one lens and/or mirror;

such that a collimated electromagnetic beam enters said first at least one lens and/or mirror, is converged and at least partially passes through said pin hole, and is re-collimated by said second at least one lens and/or mirror.

7. A spectroscopic rotating compensator ellipsometer system as in claim 1 in which compensators are present both before and after said stage for supporting a sample system, and a selection is made from the group consisting of:
- both said compensators are caused to rotate in use; and
- one of said compensators is caused to rotate in use.

8. A spectroscopic rotating compensator ellipsometer system as in claim 1 in which a optical fiber is present at least one location selected from the group consisting of:
- between said source of a polychromatic beam of electromagnetic radiation and a polarizer; and
- between said analyzer and said dispersive optics and at least one detector system which contains a multiplicity of detector elements.

9. A spectroscopic rotating compensator ellipsometer system as in claim 8 in which said optical fiber is present after said analyzer, said optical fiber becoming at least bifurcated thereby providing a plurality of optical fiber bundles, at least two of which plurality of at least two bifurcated optical fiber bundles provide input to separate detector systems, each of said separate detector systems comprising a dispersion optics and a multiplicity of detector elements, said plurality of optical fiber bundles having cross-sectional shapes at ends thereof selected from the group:
- essentially circular, essentially slit shaped;
- other than essentially circular; and
- essentially slit shaped.

10. A system for investigating samples comprising:
a) a source of a beam of electromagnetic radiation;
b) an aperture;
c) a first focusing means
d) a sample;
e) a second focusing means;
f) an optical fiber; and
g) a detector system;

such that in use said first focusing means focuses electromagnetic radiation provided by said source thereof, and which passes through said aperture, onto said sample; and
such that said second focusing means is oriented with respect to said optical fiber such that at least some electromagnetic radiation reflecting from said sample is focused thereby onto an end thereof;
such that an outer annular region of said electromagnetic beam is attenuated as it passes through said optical fiber prior to entering said detector.

11. A system as in claim 10, which further comprises an optical fiber between said source and said sample through which electromagnetic radiation is caused to pass.

12. A system as in claim 10 which further comprises a polarizer between said source of a beam of electromagnetic radiation and said sample, and an analyzer between said sample and said detector, and in which said system is an ellipsometer.

13. A system as in claim 12 which further comprises at least one compensator present at a location selected from the group consisting of:
- between said polarizer and said sample; and
- between said sample and said detector.

14. A system as in claim 10, in which the source of electromagnetic radiation is spectroscopic.

15. A system for investigating samples comprising:
a) a source of a beam of electromagnetic radiation;
b) a first optical fiber;
c) a first focusing means;
d) an aperture;

e) a sample;

f) a detector system;

such that in use said first optical fiber receives electromagnetic radiation from said source of a beam thereof and directs it to pass through said first focusing means and aperture and then onto said sample;

such that at least some of said electromagnetic radiation reflects from said sample;

said system being characterized in that it further comprises:

a second focusing means; and a second optical fiber;

which are oriented such that at least some of the electromagnetic radiation reflecting from said sample is focused by said second focusing means onto an end of said second optical fiber which carries it into said detector system;

said second optical fiber serving to cause an outer annular region of said electromagnetic beam to be attenuated as it passes therethrough, prior to entering said detector system.

16. A system as in claim 15 which further comprises a polarizer between said source of a beam of electromagnetic radiation and said sample, and an analyzer between said sample and said detector, and in which said system is an ellipsometer.

17. A system as in claim 16 which further comprises at least one compensator present at a location selected from the group consisting of:

between said polarizer and said sample; and between said sample and said detector.

18. A system as in claim 15, in which the source of electromagnetic radiation is spectroscopic.

19. A system for investigating samples comprising:

a) a source of a beam of electromagnetic radiation;

b) a first optical fiber;

c) a collimating means;

d) an aperture:

e) a first focusing means;

f) a sample;

g) a second focusing means;

h) a second optical fiber; and f) a detector system;

such that in use said first optical fiber receives electromagentic radiation from said source of a beam thereof and directs it to pass through said collimating means, aperture, first focusing means and then onto said sample; and such that said second focusing means is oriented with respect to said optical fiber such that at least some electromagnetic radiation reflecting from said sample is focused thereby onto an end thereof;

such that an outer annular region of said electromagnetic beam is attenuated as it passes through said optical fiber prior to entering said detector.

20. A system as in claim 19 which further comprises a polarizer between said source of a beam of electromagnetic radiation and said sample, and an analyzer between said sample and said detector, and in which said system is an ellipsometer.

21. A system as in claim 20 which further comprises at least one compensator present at a location selected from the group consisting of:

between said polarizer and said sample; and between said sample and said detector.

22. A system as in claim 19, in which the source of electromagnetic radiation is spectroscopic.

23. A system for investigating a sample comprising:

a) a source of a beam of electromagnetic radiation;

b) means for focusing said beam of electromagnetic radiation to said sample;

c) a detector for receiving said beam after it interacts with said sample;

said system further comprising:

d) an optical fiber positioned along the path of the beam; and e) a focusing means oriented with respect to said optical fiber such that at least some electromagnetic radiation from said focusing means is focused thereby onto an end of said optical fiber thereby;

such that an outer annular region of said electromagnetic beam is attenuated as it passes through said optical fiber.

24. A system as in claim 23 in which said optical fiber and focusing means is positioned before said sample.

25. A system as in claim 23 in which said optical fiber and focusing means is positioned after said sample.

26. A system as in claim 25 in which further comprises at least one additional focusing means positioned at a selection from the group consisting of:

before said sample; and after said sample.

27. A system as in claim 26 which further comprises an optical fiber in combination with said at least one additional focusing means positioned at a selection from the group consisting of:

before said sample; and after said sample.

28. A system as in claim 23 which further comprises a polarizer between said source of a beam of electromagnetic radiation and said sample, and an analyzer between said sample and said detector, and in which said system is an ellipsometer.

29. A system as in claim 23 which further comprises at least one compensator present at a location selected from the group consisting of:

between said polarizer and said sample; and between said sample and said detector.

* * * * *